(12) United States Patent
Okuda et al.

(10) Patent No.: US 8,529,634 B2
(45) Date of Patent: Sep. 10, 2013

(54) PROSTHETIC LIMBS WITH MEANS CAPABLE OF REDUCING TORQUE IN THE INITIAL PERIOD OF BEND OF KNEE JOINT

(75) Inventors: Masahiko Okuda, Kobe (JP); Yoshiaki Nakaya, Kobe (JP)

(73) Assignee: Nabtesco Corporation, Tokyo (JP)

( * ) Notice: Subject to any disclaimer, the term of this patent is extended or adjusted under 35 U.S.C. 154(b) by 438 days.

(21) Appl. No.: 12/531,542

(22) PCT Filed: Mar. 16, 2007

(86) PCT No.: PCT/JP2007/055341
§ 371 (c)(1),
(2), (4) Date: Sep. 16, 2009

(87) PCT Pub. No.: WO2008/114340
PCT Pub. Date: Sep. 25, 2008

(65) Prior Publication Data
US 2010/0049334 A1 Feb. 25, 2010

(51) Int. Cl.
*A61F 2/64* (2006.01)
(52) U.S. Cl.
USPC .......................................................... 623/44
(58) Field of Classification Search
IPC .................................. A61F 2/642,2/644, 2/646
See application file for complete search history.

(56) References Cited

U.S. PATENT DOCUMENTS

| 5,181,931 A | 1/1993 | van de Veen |
| 5,888,237 A | 3/1999 | Shiraishi et al. |
| 6,086,616 A | 7/2000 | Okuda et al. |
| 6,508,843 B2 * | 1/2003 | Suzuki .......................... 623/46 |
| 6,558,430 B1 | 5/2003 | Nakaya et al. |

FOREIGN PATENT DOCUMENTS

| GB | 1 533 796 | * 11/1978 |
| JP | 05-000146 A | 1/1993 |
| JP | 11-128257 A | 5/1999 |
| JP | 11-285508 A | 10/1999 |
| JP | 2001-137268 A | 5/2001 |
| JP | 2002-058689 A | 2/2002 |

* cited by examiner

*Primary Examiner* — David H Willse
(74) *Attorney, Agent, or Firm* — Frommer Lawrence & Haug LLP; Ronald R. Santucci

(57) ABSTRACT

A technology for making the sensation at use of prosthetic limbs utilizing a hydraulic cylinder and a spring cylinder as comfortable as at use of those utilizing a pneumatic cylinder and further for improving walk following properties. In particular, the arrangement of a hydraulic cylinder or a spring cylinder, or the like, is specified. Accordingly, the resistance produced by the hydraulic cylinder or spring cylinder in accordance with an increase of knee angle is increased, The first torque T1 at the first stage of initial period of bend of the knee joint is made small, while the second torque T2 at the second stage of final period of the further advanced bend of knee joint is made large, thereby satisfying a relation of $T1 \geqq T2$, as different from conventional ones.

7 Claims, 20 Drawing Sheets

$\theta s = 10°$ $\theta s = 20°$ $\theta s = 30°$

40°

60°

20°

40°

60°

PROSTHETIC LIMBS WITH MEANS CAPABLE OF REDUCING TORQUE IN THE INITIAL PERIOD OF BEND OF KNEE JOINT

This application is a 371 of PCT/JP2007/055341 filed on Mar. 16, 2007, published on Sep. 25, 2008 under publication number WO 2008/114340 A, the disclosure of which is hereby incorporated by reference.

TECHNICAL FIELD

This invention relates to a prosthetic limb equipped with drag generating means for producing a resistance or drag, such as a hydraulic cylinder or a spring cylinder ("spring cylinder" used herein may include those provided, either inside or outside the hydraulic cylinder or the pneumatic cylinder, with a spring for acting a force on a piston for assisting extension of knee joint), in response to bending or extending movements of the leg through the knee joint, and more particularly to a technology for improving walk following properties while reducing a force acting on the prosthetic limb through its wearer (e.g., the user of the prosthetic limb) when the toe is separated from the ground surface at the time of walking.

BACKGROUND ART

The prosthetic limb provided with a knee joint normally includes drag generating means such as a pneumatic cylinder, a hydraulic cylinder or a spring cylinder, in order to make effective movements through the knee joint. The pneumatic cylinder has such features that the initial resistance produced at the beginning of bend of knee joint is small and therefore, the burden received by the wearer's hip joint muscle is small. However, since pneumatic pressure is compressed, the force produced by the pneumatic cylinder is smaller than that produced by the hydraulic cylinder or the spring cylinder. Therefore, in order to obtain a force large enough for the prosthetic limb, the size of the pneumatic cylinder must be larger than a certain size. The size-increase of the pneumatic cylinder is inconvenient when a small-sized prosthetic limb is to be made.

On the other hand, the hydraulic cylinder uses oil that is an incompressible fluid and therefore, it can produce a force larger than that of the pneumatic cylinder. The spring cylinder can also produce a force larger than that of the pneumatic cylinder in compliance with the spring constant. Thus, the hydraulic cylinder and the spring cylinder are more advantageous than the pneumatic cylinder from the standpoint of making a small-sized prosthetic limb. On the other hand, the hydraulic cylinder and the spring cylinder have such drawbacks that the prosthetic limb wearer must withstand an increased burden received by his/her hip joint. Because of the reasons just mentioned, use of the prosthetic limb equipped with the hydraulic cylinder is limited to those persons who have strong muscle and body. By reducing the spring force, the prosthetic limb equipped with the spring cylinder can be used by those persons who have comparatively weak muscle and body. However, the prosthetic limb equipped with the spring cylinder having a reduced spring force is not suitable for those who have a strong muscle and body.

For example, Patent Document 1 shows a prosthetic limb equipped with a pneumatic cylinder, Patent Document 2 shows a prosthetic limb equipped with a hydraulic cylinder and Patent Document 3 shows a prosthetic limb equipped with a spring cylinder.

Patent Document 1: Japanese Patent Application Laid-Open No. 2001-137268
Patent Document 2: Japanese Patent Application Laid-Open No. 2002-58689
Patent Document 3: Japanese Patent Application Laid-Open No. S55-130657

DISCLOSURE OF THE INVENTION

Problem to be Solved by the Invention

The inventors of the present invention have paid attention to the hydraulic cylinder and the spring cylinder which are advantageous in making a small-sized prosthetic limb and have made extensive search and development with regard to the characteristics obtainable between knee angle and resistance (drag or rotational torque). FIG. 1 shows one cycle of a walking form by a wearer of the prosthetic limb (generally called "above knee prosthesis"). The one-cycle of a walking form of a prosthetic limb wearer includes a swing phase where the foot is in the air and not in contact with the ground surface and a stance phase where the foot is in contact with the ground surface. In this one-cycle, the prosthetic limb wearer makes his/her hip joint muscle (Ma, Mb and Mc) work three times. The first time is in a period when the knee starts bending with the toe contacting the ground surface (see S0 of FIG. 1), the second time is in a period when the leg that is bent maximum is about to swing forward (see S1 of FIG. 1) and the third time is in a period when a stance phase is about to be achieved with the heel contacting the ground surface (see S2 of FIG. 1). Of the total three periods, in the third period when the stance phase is about to be achieved, the above knee prosthesis wearer can cope with the situation utilizing the force caused by his/her weight. In contrast, the force caused by the wearer's weight is not large enough at the beginning of bent of knee joint or in the initial period of the first swing phase and in the final period of bent of the second swing phase. Therefore, the wearer must make his/her hip joint muscle (Mc, Ma) work actively.

Examining the resistance (drag or rotational torque) produced by the hydraulic cylinder or the spring cylinder with respect to the conventional prosthetic limbs utilizing a hydraulic cylinder or a spring cylinder, we have found a certain common point. The common point is that the resistance is large in the period of S0 of FIG. 1 when the bending angle is small and the resistance is small in the period of S1 of FIG. 1 when the bending angle is large. It can be considered that the hydraulic cylinder or the spring cylinder is merely arranged in a vacant space without any technical intention or it is arranged in place with an intention for making large of the extending function of a spring in order to prevent the knee from bending in the third period. Knee bending occurs when the knee extension by the hip joint muscle is not large enough.

Thus, the conventional prosthetic limb utilizing drag generating means such as a hydraulic cylinder or a spring cylinder has such drawbacks that a large burden received by the hip joint muscle (Mc) is required in order to overcome a large resistance produced by the drag generating means in the initial period of bend of knee joint, and that the prosthetic limb is excessively swung up and a long time is required for the prosthetic limb to return to its original position because the resistance is small at the time when the toe is separated from the ground surface and the knee angle is increased, thus resulting in poor walk following properties. In order to obtain favorable walk following properties for the prosthetic limb, a large hip joint muscle (Ma) is required to work. Therefore, the wearer easily gets tired due to a large burden received by the hip joint muscle (Mc, Ma), and the sense of comfortable use of the prosthetic limb is impaired.

Many attempts can, of course, be made in order to improve the sense of use of the prosthetic limb. For example, the opening rate of a throttle valve installed inside the hydraulic cylinder may be controlled by a microcomputer, or the throttling amount of the hydraulic cylinder may be varied by steppingly varying the number of hydraulic flow passage in accordance with the position of the piston, or the spring force of the spring cylinder may be mechanically varied. However, any of the above-mentioned constitutions is complicated and results in cost-increase of the prosthetic limb.

It is, therefore, an object of the present invention to provide a technology capable of making the sensation at use of a prosthetic limb utilizing a hydraulic cylinder and a spring cylinder as comfortable as at use of that utilizing a pneumatic cylinder and also capable of improving walk following properties without such cost increase as mentioned above.

The present invention provides a prosthetic limb utilizing a hydraulic cylinder or a spring cylinder and capable of properly increasing a resistance produced by the hydraulic cylinder or the spring cylinder in accordance with an increase of knee angle.

Other objects of the present invention will become more manifest from the detailed description to follow.

Means to Solve the Problem

According to the present invention, a resistance (or a drag) produced by the drag generating means is increased by specifying the arrangement of the drag generating means, such as a hydraulic cylinder and a spring cylinder, per se, instead of by a method for controlling the opening rate of a throttle valve installed inside a hydraulic cylinder or by a method for varying the throttling amount of a hydraulic cylinder in accordance with the position of a piston or for mechanically varying the spring force of a spring cylinder. A prosthetic limb incorporated with the present invention is composed of a multiple-link mechanism, and it comprises a knee joint for making an upper member and a lower member movable about the center of rotation and drag generating means pivotally attached to the multiple-link mechanism and adapted to produce a drag for restraining deformation of the multiple-link mechanism. The prosthetic limb utilizing a hydraulic cylinder or a spring cylinder as drag generating means can produce a larger drag per unit area than that utilizing a pneumatic cylinder, and it can, therefore, be helpful for making compact of the prosthetic limb. Moreover, the prosthetic limb utilizing a hydraulic cylinder or a spring cylinder can cope with a wide range of walk forms from a normal slow walk to a tripping walk.

The present invention is related to a prosthetic limb including a knee joint which is composed of a multiple-link mechanism. The knee joint composed of the multiple-link mechanism is variable in the center of rotation and can, therefore, produce movements more similar to those of walking by a healthy person. The multiple-link mechanism has normally four links but it may include five or six links by additionally employing an auxiliary link for stabilizing a stance posture or assisting extension of the leg. The present invention may also be applied to such a multiple-link mechanism having a number of links equal to or larger than four links including such an auxiliary link as mentioned above. The multiple-link mechanisms having a number of links equal to or larger than four links are common in that they include at least two links, namely, a front link located on a front side of the knee and a rear link located on a rear side of the knee. In the description to follow, description is made mostly on a four-link mechanism as a basic multiple-link mechanism. It should be noted, however, that the multiple-link mechanism to which the present invention is applicable, is not limited to the four-link mechanism.

Characteristics between knee angle and torque (resistance or drag produced by hydraulic pressure or spring) that are the main theme of the present invention will be described first. FIGS. 2A and 2B show a characteristics curve wherein knee angle is plotted along the abscissa and torque is plotted along the ordinate. The conventional hydraulic cylinder of FIG. 2A has such characteristics that torque is large at the first stage where the knee angle is small and torque is gradually increased in accordance with the further advanced increase of knee angle. In contrast, the hydraulic cylinder of the present invention shown in FIG. 2B has such characteristics that the torque is small at the first stage where the knee angle is small and the torque is gradually increased in accordance with the further advanced increase of knee angle. There are some occasions that the torque is large around the area of knee angle 0°. However, since the force produced by the prosthetic limb wearer's weight is larger than the torque in the nearby area of knee angle 0°, the burden received by the prosthetic limb wearer is not so large. Moreover, the torque is increased as the knee angle is further increased and it reaches a peak at a certain knee angle. Thereafter, the moving speed of the piston of the hydraulic cylinder becomes slow at a certain knee angle larger than 60° that is the maximum bending angle of knee joint when the wearer is in a normal walking form. Since the hydraulic cylinder produces a drag which is proportional to two powers of this moving speed, the drag produced by the hydraulic cylinder and thus, the torque is greatly reduced. However, this offers practically no problem because the moving speed of the piston becomes slow only when the bending angle is larger than the maximum bending angle when the wearer is in a normal walking form.

In comparison with such hydraulic cylinder, the spring cylinder produces a drag (repulsive force) proportional to its overall length and it is not affected by the moving speed of the piston. FIGS. 3A and 3B show a characteristic curve between knee angle and torque obtainable when the spring cylinder is utilized. The conventional spring cylinder shown in FIG. 3A exhibits, as in the case with the conventional hydraulic cylinder, such characteristics that the torque is large at the first stage where the knee angle is small and the torque is gradually decreased in accordance with the increase of knee angle. In contrast, the spring cylinder of the present invention shown in FIG. 3B shows, as in the case with the hydraulic cylinder of the present invention, such characteristics that the torque is small at the first stage where the knee angle is small and the torque is gradually increased in accordance with the increase of knee angle. Moreover, this spring cylinder provides such additional characteristics that the torque is increased even when the bending angle of knee joint become larger than 60° that is the maximum bending angle when the wearer is walking in a normal walking form.

A resistance (or drag) produced by the drag generating means such as the hydraulic cylinder or spring cylinder is a torque T about the instantaneous center of rotation determined by the multiple-link mechanism. The torque T is a product of the distance from the action line of the force produced by the drag generating means to the center of rotation, i.e., the length L of the lever arm and the force F produced by the drag generating means. Accordingly, the torque T can be varied by controlling the length L of the lever arm and the force F produced by the drag generating means.

According to the present invention, the first torque T1 at the first stage of initial period of bend of knee joint is made small, while the second torque T2 at the second stage of final period of the further advanced bend of knee joint is made large in order to reduce the burden received by the hip joint muscle (Mc) in the initial period of bend of knee joint and in order also to improve the walk following properties. It is preferable that a relation of T1<T2 is satisfied in order to more effectively reduce the burden received by the prosthetic limb wearer. Since the relation is conventionally T1>T2, the burden received by the hip joint muscle (Mc, Ma) of the wearer can be reduced by realizing at least the relation of T1≦T2. Although the knee bending angle at the first stage of initial period of bend of knee joint is smaller here than that at the second stage of final period of bend of knee joint, the knee angle at each stage is different depending on individual wearers. Normally, the knee angle at the first stage of initial period of bend of knee joint is in a range from 0° to 45°, and the knee angle at the second stage of final period of bend of knee joint is in a range from 45° to 60°.

The first technological significance of the present invention is to provide a novel prosthetic limb which satisfies the relation of T1≦T2. According to the novel prosthetic limb of the present invention, the torque T1 produced at the first stage of initial period of bend of knee joint is relatively small. This torque T1 is small enough even compared with the torque produced by the wearer's weight (see FIG. 4). Accordingly, the load occurrable in the initial period of bend of knee joint is not felt as a burden by the wearer. One example when felt by the wearer as a burden at the time of bend of knee joint according to the present invention can be obtained from the characteristics curve o, shown in a solid line of FIG. 4. Likewise, one example when felt by the wearer as a burden can be known from the characteristics curve a, shown in a broken line of FIG. 4. The first advantage of the present invention will become manifest from the comparison between those two characteristics curves o and a, i.e., such a basic advantage that in spite of utilizing a hydraulic cylinder or a spring cylinder in the present invention, the load felt by the wearer as a burden in the initial period of bend of knee joint can be reduced to the size when a pneumatic cylinder is utilized. In the final period of bend of knee joint, however, since the torque T2 is relatively increased, the knee is not excessively bent. Accordingly, comfortable walk following properties can be obtained. This is the second advantage of the present invention.

The second technological significance of the present invention for providing such a novel prosthetic limb as mentioned above, resides in a method for specifying the arrangement of the drag generating means, such as a hydraulic cylinder or a spring cylinder, more particularly a method for specifying the attachment position of the drag generating means with respect to a multiple-link mechanism that constitutes the knee joint. Since the present invention provides a method for specifying the arrangement of the drag generating means, the constitution of the drag generating means, per se remains same as that of the related art and thus, no complicated constitution is required. A plurality of methods may be employed as a concrete method for specifying the arrangement.

The first method for specifying the arrangement is achieved by an idea for paying attention to the length L of the lever arm. The length L1 of the lever arm at the first stage of initial period of bend of knee joint is made smaller than the length L2 of the lever arm at the second stage of final period of bend of knee joint. In other words, a relation of L1<L2 is satisfied. It is preferable that the length L of the lever arm at an arbitrary angle in the initial period of bend of knee joint is set to zero (0). By doing so, after this angle, the length L of the lever arm is increased until the walking form is advanced into the final period of bend of knee joint. Thus, a relation of L1<L2 can necessarily be obtained. FIG. 5 diagrammatically shows the first method. In FIG. 5, the four-link mechanism 10 is in a state of the initial period of bend of knee joint wherein the bending angle θs is in the range of 0°<θs<45°. The bending angle θs is a knee angle in the initial period of bend of knee joint where the drag is desired to be made small. The bending angle θs is normally about 20°, though it is slightly depending on individual wearers of the prosthetic limb. The four-link mechanism 10 comprises four links, namely, a link 12 corresponding to the upper member, a link 14 corresponding to the lower member, a front link 16 and a rear link 18. The drag generating means is attached to the multiple-link mechanism 10 at two spots, e.g., one at a link 12 corresponding to the upper member and the other at a link 14 corresponding to the lower member.

A straight line is 1s obtained as shown in FIG. 5, which straight line is passes through the instantaneous center Os of rotation of the four-link mechanism 10 at the bending angle θs and the upper attachment position Ps of the drag generating means. According to the idea of the first method of the present invention, the lower attachment position Qs of the drag generating means is arranged on this straight line 1s. According to the arrangement based on this idea, since the length L of the lever arm at the knee bending angle θs is zero (0), the torque is also zero (0) at that time. The upper attachment position Ps of the drag generating means is arranged between the respective connection points 26, 28 which connect the front and rear links 16, 18 with the link 12 corresponding to the upper member, and thus, normally on a member which constitutes the upper member. In contrast, the lower attachment position Qs of the drag generating means is arranged on the straight line Qs and between the respective connection lines 46, 48 which connect the front and rear links 16, 18 with the link 14 corresponding to the lower member, but when the bending angle θs is about 20° that is the normal bending angle, the lower attachment position Qs is arranged above the height position which connects the two A connection points 46, 48 to each other. In practice, the lower attachment position Qs and the upper attachment position Ps of the drag generating means are arranged on the straight line 1s while avoiding interference with the members which constitute the respective links and other peripheral parts. What is required for the lower attachment position Qs and the upper attachment position Ps is located on the straight line 1s and so, they may be located above the link 12 corresponding to the upper member or under the link 14 corresponding to the lower member.

In order to further reduce the burden felt by the prosthetic limb wearer in the initial period of bend of knee joint, it is effective that the bending angle θs is made smaller. FIG. 6A shows the characteristics obtainable when the bending angle θs is set approximately to 20° that is the normal bending angle. In contrast, FIG. 6B shows the characteristics obtainable when the bending angle θs is set to 5°. It will be understood from those Figures that the torque felt by the wearer as a burden, can be reduced by making the bending angle θs smaller. However, when the torque is made excessively small in the initial period of bend of knee joint (for example, when the bending angle θs is set to 5°), the torque obtainable at the time of extension of knee joint (see FIG. 4) is also small. As a result, it gives rise to such problems that a terminal impact (namely, the impact occurrable when the piston hits the bottom of the cylinder vigorously) that is likely to occur by the torque produced by the drag generating means at the time of extension of knee joint, is difficult to restrain. By employing other known means (for example, a cushion member provided to the bottom part of the cylinder) for restraining the terminal impact, the bending angle θs may be set smaller (for example, 10° or even smaller) than the normal 20°. In order to further simplify the constitution, however, it is desired that by selecting the set value of the bending angle θs (preferably a value that is larger than 10° but smaller than 20°), the terminal impact caused by the torque produced by the drag generating means at the time of extension of knee joint is restrained. It should be noted that when the bending angle θs at which the length L of the lever arm is desired to make zero (0) is made small, the lower attachment position Qs of the drag generating means is further lowered in height position and thus, much difficulty is encountered for the drag generating means to avoid interference with other parts.

According to the first method of the present invention, the length of the lever arm in the initial period of bend of knee joint where the drag is desired to be made small is set to zero (0), thereby reducing the torque produced by the drag generating means. According to the second method of the present invention, attention is also paid to the moving speed of the piston of the drag generating means while employing the entire constitution of the first arrangement method. FIG. 7 diagrammatically shows the second method of the present invention. According to the second method, the lower attachment position Qs of the drag generating means is arranged on the straight line 1s at the time when the bending angle θs is, for example, about 20°. This procedure is same as in the first method. In addition to that, according to the second method of the present invention, the lower attachment position Qs is more strictly specified to a particular point Qi. A smaller bending angle θo (for example, 0°) than the bending angle θs is selected and the upper attachment position of the drag generating means at that time is represented by Po. According to the second method, the particular point Qi located on the straight line 1s and equidistant from the upper attachment position Ps at the larger bending angle θs and the upper attachment position Po at the smaller bending angle θo is determined as the lower attachment position of the drag generating means. By specifying the lower attachment position in such a manner as just mentioned, the overall length of the drag generating means can be almost fully prevented from being varied at the time when the knee angle is varied from the smaller bending angle θo to the larger bending angle θs. Accordingly, the drag generating means does not produce the force F during such bending period and the torque that is a resistance, is hardly fluctuated. As the prosthetic limb including the knee joint, a hip prosthesis is known besides the above knee prosthesis. In case of the hip prosthesis, torque caused by the wearer's weight in the initial period of bend of knee joint is more difficult to produce than in the case with the above knee prosthesis. Accordingly, this second method of the present invention is more advantageously applicable to the hip prosthesis rather than to the above knee prosthesis.

By means of the first and second methods mentioned above, the length L1 of the lever arm at the first stage of the initial period of bend of knee joint can be made smaller than the length L2 of the lever arm at the second stage of final period of bend of knee joint, or a relation of T1<T2 can be satisfied between the first torque T1 at the first stage and the second torque T2 at the second stage. For example, when the lower attachment position of the drag generating means is set to the point Qi according to the second method, the relation between the knee angle and the lever arm can be shown by the characteristics curve qi shown in a broken line of FIG. 8. What is further demanded with respect to the characteristics curve qi is that production of the torque at the beginning of bend is made gentle and a rise of torque is not excessively increased between the torque near the bending angle θs and the torque at the portion where the bending angle is larger (for example, 30° through 40°) than the bending angle θs. When a large torque is suddenly produced in a state where no torque is produced at the beginning of bend, the wearer feels the change of torque sensitively. In order to make him/her feel comfortable, it is preferable to avoid an abrupt production of torque. Moreover, when a steep rise of torque occurs in the range of area from the nearby area of the bending angle θs where a small drag is desired, to the area where the bending angle is increased, a hydraulic resistance, for example, is abruptly increased with a result of generation of an impact sound. Generation of such impact sound is preferably prevented from occurring.

In order to respond to the above-mentioned requirement, according to the third method, the lower attachment position of the drag generating means is slightly positionally adjusted from the point Qi to a point Q. The range of the point Q where the position can be adjusted is shown, for example, by a mesh section m in FIG. 9. The point Q within the mesh section m is located near the point Qi that is the reference point, and a relation of Ls<L60 is satisfied at the point Q, where Ls is the length of the lever arm at the bending angle θs and L60 is the length of the lever arm at a larger bending angle (for example, 60°) than the bending angle θs. When the lower attachment position of the drag generating means is adjusted to the point Q within the mesh section m with respect to the point Qi, the relation between the knee angle and the length of the lever arm is as shown by the characteristics curve q shown in a broken line in FIG. 8. The characteristics curve q after positional adjustment in comparison with the characteristics curve q1 before positional adjustment has such characteristics that the generation of torque at the beginning of bend of knee joint is gentle and the rise of torque at larger bending angles than the bending angle θs is eased. FIGS. 10A through 10C show how the location of the mesh section M is fluctuated depending on the size of the bending angle θs. The mesh section m is likely to move upward as the bending angle θs is increased. For example, there is a distance of about 40 mm in a vertical direction between the mesh section of FIG. 10A and the mesh section of FIG. 10C. As means for adjusting the lower attachment position of the drag generating means, such function of a spring as being capable of converting a rotational motion to a linear motion may be utilized so that the attachment position can be continuously moved, or a plurality of attachment positions may be preliminarily prepared so that the positional adjustment can be made by properly selecting one of the attachment positions. Instead of the lower attachment position of the drag generating means, the upper attachment position may be adjusted.

In the following, description will be made more specifically how the characteristics between the knee angle and the torque are affected when the lower attachment position of the drag generating means is adjusted. For example, when the lower attachment position is moved on the straight line 1s, the torque at the beginning of bend of knee joint is fluctuated. The torque at the beginning of bend of knee joint is increased as the lower attachment position is moved from the reference point Qi toward the upper attachment position. Conversely, when the lower attachment position is moved in a direction away from the upper attachment position, the torque at the beginning of bend of knee joint is likely to decrease. Moreover, when the lower attachment position is moved on the straight line 1s, the rise of torque is scarcely affected in the range of area from the nearby area of the bending angle θs to the area where the bending angle is increased. In contrast, when the lower attachment position is moved in a direction orthogonal to the straight line 1s instead of on the straight line, the rise of torque in the range of area from the nearby area of the bending angle θs to the area where the bending angle is increased, is varied. The rise of torque is likely to become gentle by finely adjusting the lower attachment position in a direction toward the connection point 46 between the line 14 corresponding to the lower member and the front link 16. At any rate, the torque in the initial period of bend of knee joint and the torque in the final period of bend of knee joint can be balanced by adjusting the lower attachment position from a particular reference point Qi on the straight line 1s to a point in its peripheral area.

When the drag generating means is a hydraulic cylinder, the torque at the time of bend of knee joint and the torque at the time of extension of knee joint are independently adjusted by utilizing two throttle valves in normal practice. It is, therefore, preferable that the point Q is arranged on the right side, in the Figures, of the straight line 1s within the mesh section m. When the point Q is arranged on the left side of the straight line 1s, the torque is affected by the throttle valves used for extension even at the time of bend of knee joint because of the relation with the lever arm and thus, the torque at the time of extension of knee joint and the torque at the time of bend of knee joint are difficult to adjust independently.

DESCRIPTION OF REFERENCE NUMERALS

Figure 1:
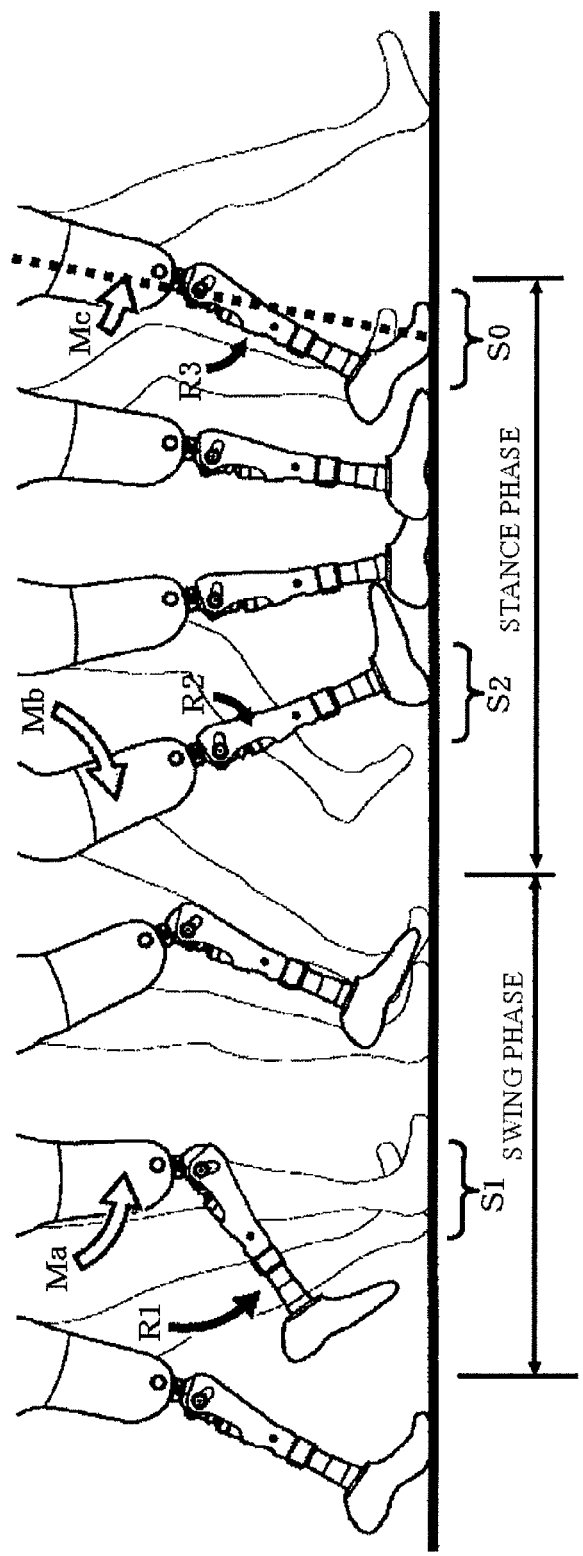
FIG. 1 shows one cycle of a walking form according to one embodiment of a prosthetic limb.

10 . . . four-link mechanism
12 . . . link corresponding to the upper member
14 . . . link corresponding to the lower member
16 . . . front link
18 . . . rear link
θs . . . knee angle at the initial stage of bend of knee joint where drag force is to be made small
Ps . . . upper attachment position of the drag generating means
Qs . . . lower attachment position of the drag generating means
Qi . . . reference point
m . . . position adjustable range (mesh section) of the point Q
50 . . . prosthetic limb (above knee prosthesis)
52 . . . upper member
54 . . . lower member
56 . . . front link
58 . . . rear link
60 . . . knee joint
70 . . . hydraulic cylinder
70 . . . hydraulic cylinder

BEST MODE FOR CARRYING OUT THE INVENTION

Figure 11A:
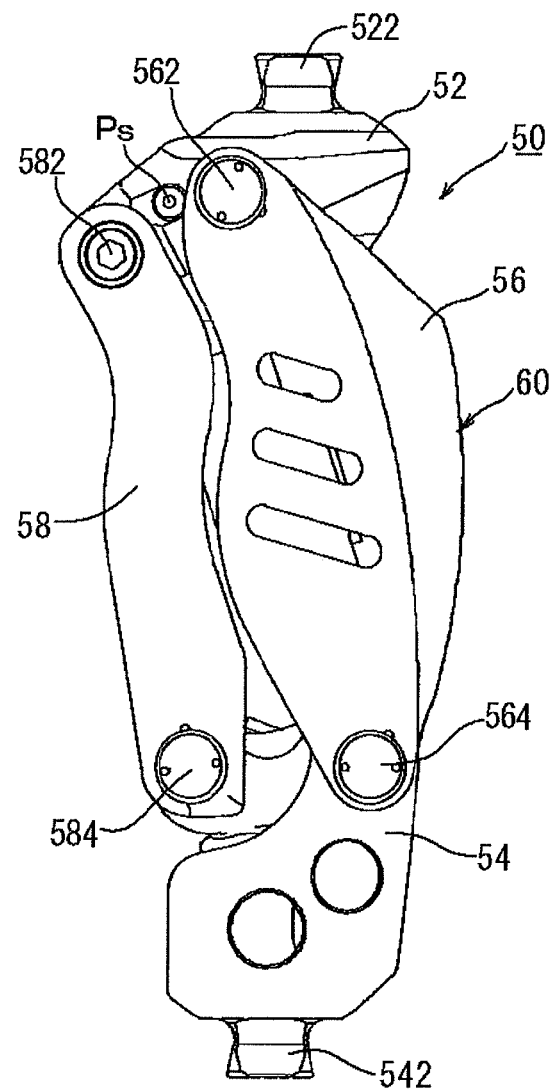
FIG. 11A is a front view showing one embodiment of a prosthetic limb according to the present invention.
Figure 11B:
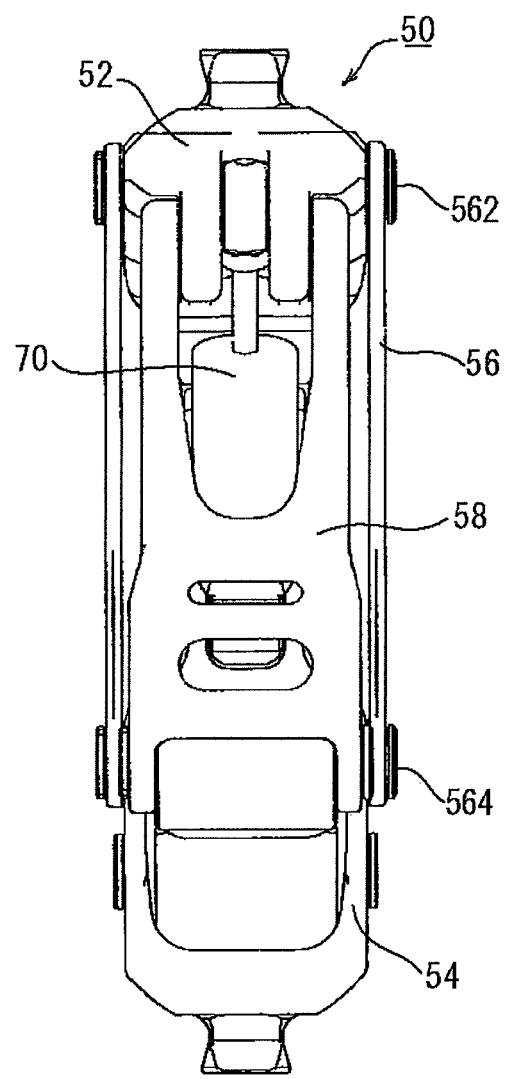
FIG. 11B is a side view of the embodiment of FIG. 11A.
Figure 11C:
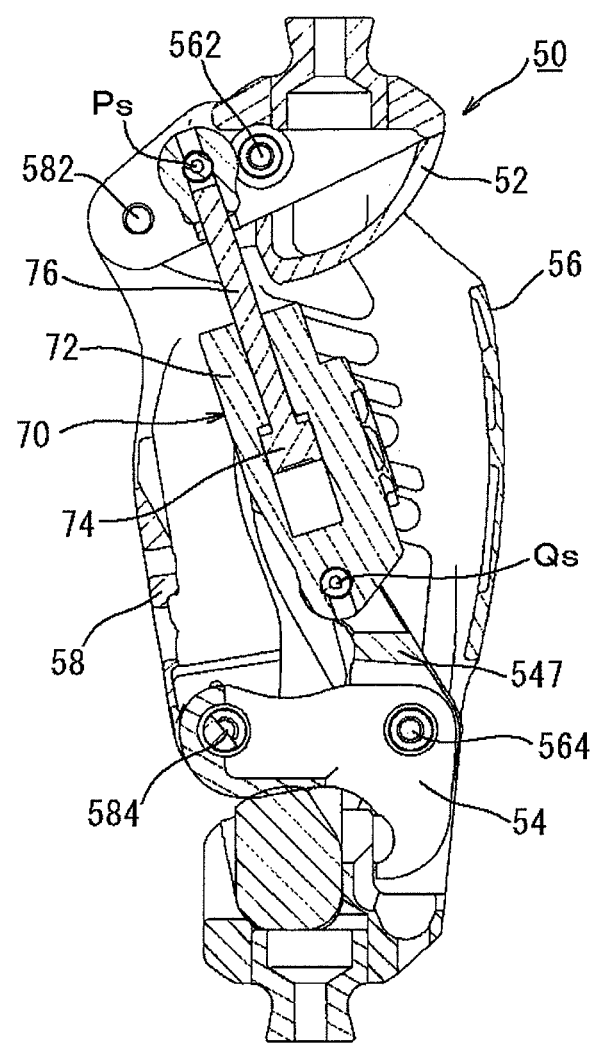
FIG. 11C is a sectional view of the embodiment of FIG. 11A.
Figure 12A:
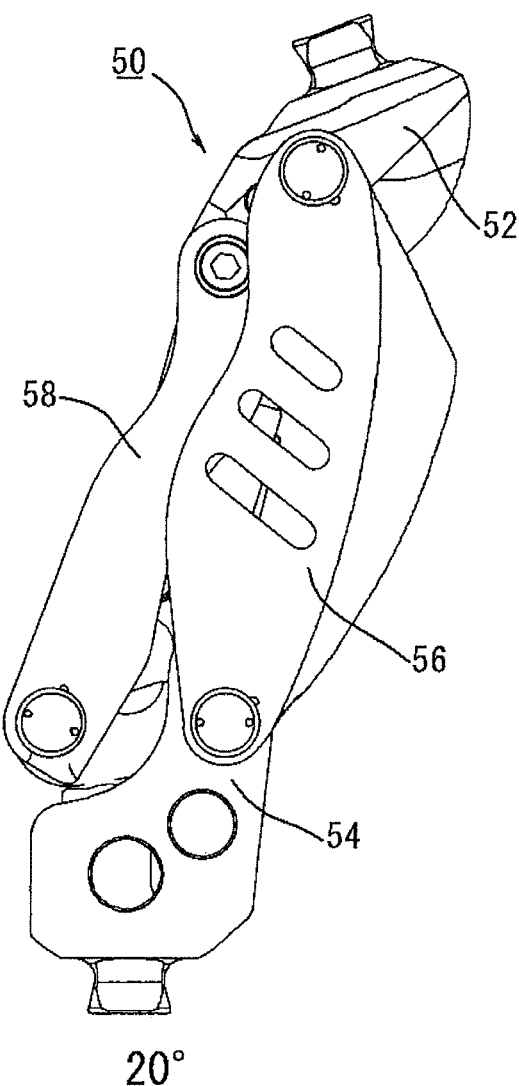
FIG. 12A is a view when the knee angle 0° of FIG. 11A is brought to 20°.
Figure 12B:
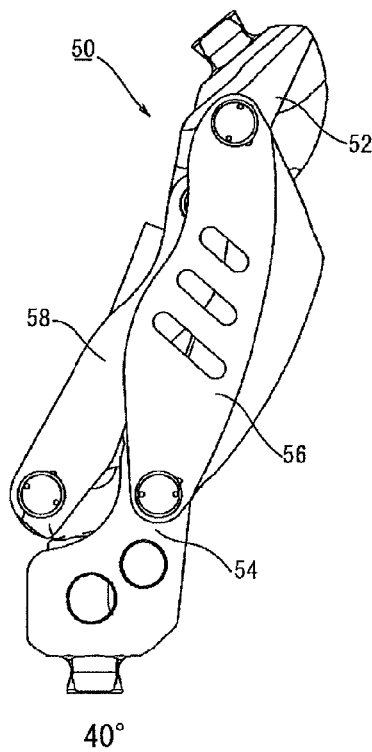
FIG. 12B is a view when the knee angle 0° of FIG. 11A is brought to 40°.
Figure 12C:
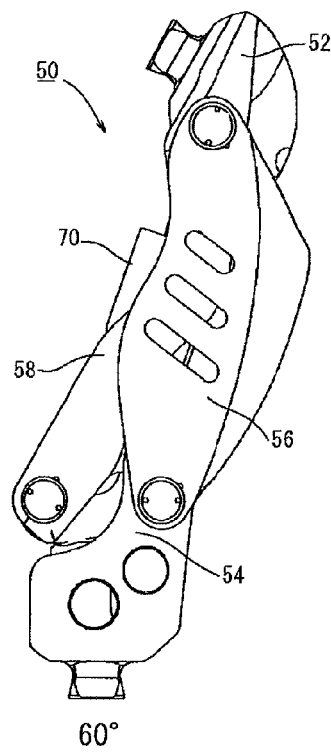
FIG. 12C is a view when the knee angle 0° of FIG. 11A is brought to 60°.
Figure 13A:
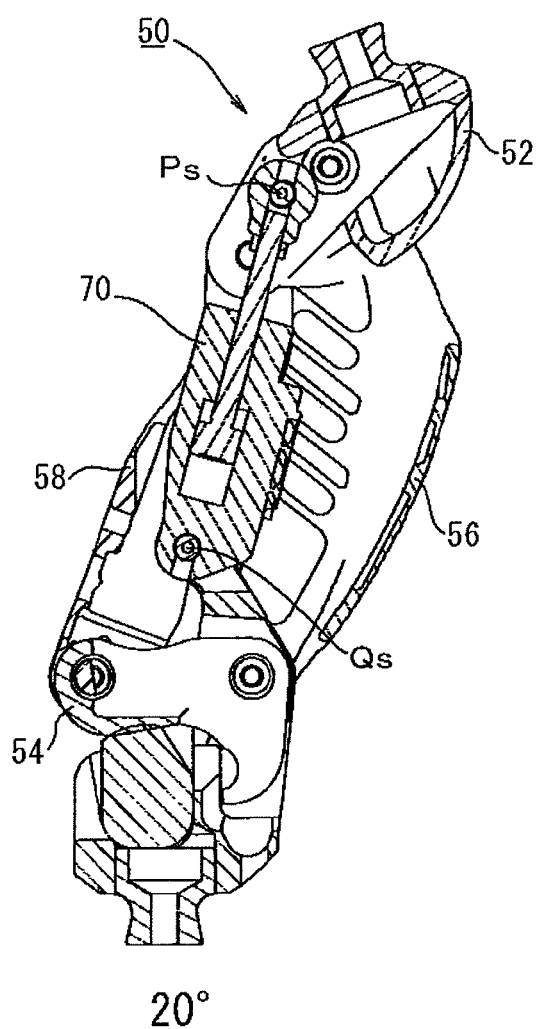
FIG. 13A is a view when the knee angle 0° of FIG. 11C is brought to 20°.
Figure 13B:
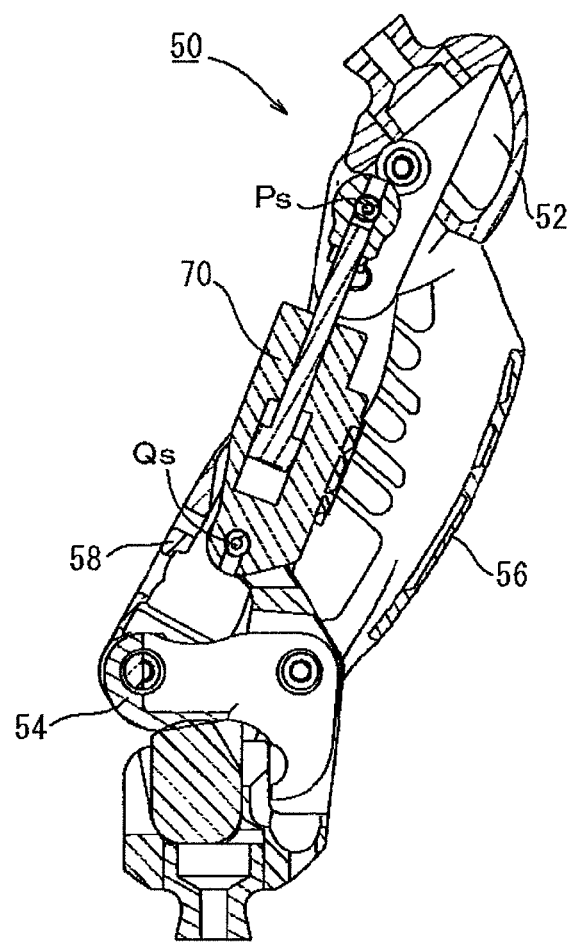
FIG. 13B is a view when the knee angle 0° of FIG. 11C is brought to 40°.
Figure 13C:
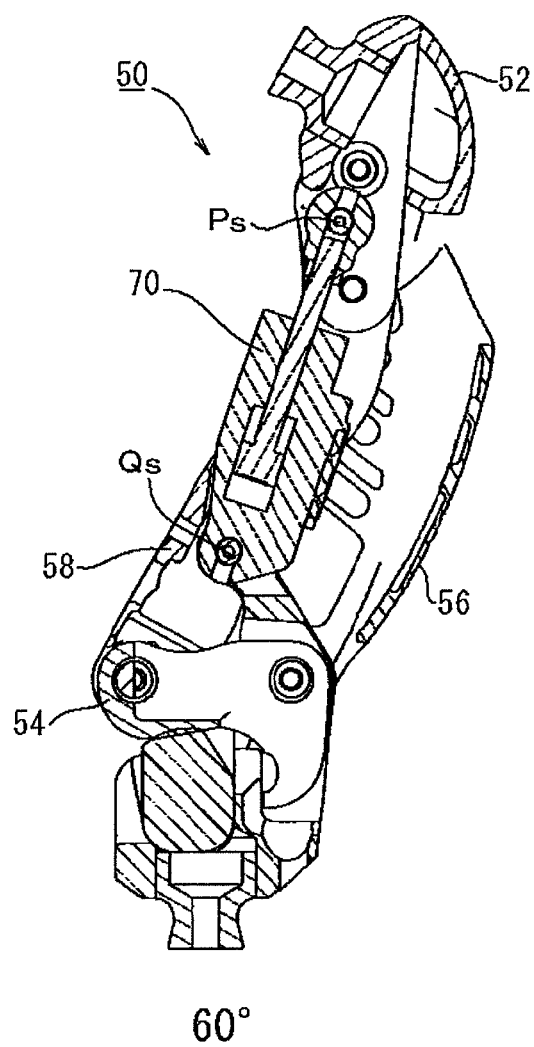
FIG. 13C is a view when the knee angle 0° of FIG. 11C is brought to 60°.

FIGS. 11A through 11C show one embodiment of a prosthetic limb according to the present invention and show, in particular, the area around the knee joint. A prosthetic limb 50, that is an above knee prosthesis, comprises an upper member 52 disposed on an upper side of the knee and a lower member 54 disposed on a lower side of the knee and pivotably coupled to the upper member 52 such that the knee can be bent. The upper member 52 integrally supports an alignment block 522 at an upper central part thereof. This alignment block 522 is adapted to attach a socket, not shown, and to withstand the load of the wearer of the prosthetic limb through the above knee prosthetic part that is received in the socket. Another alignment block 542 is disposed at a lower central part of the lower member 54. This alignment block 542 is adapted to attach a leg member that is adapted to support the foot.

The upper member 52 and the lower member 54 are coupled to each other through the knee joint 60. The knee joint 60 comprises a four-link mechanism. The four-link mechanism is a constrained chain composed of four links which are rotatably coupled to each other. Each of the upper member 52 and the lower member 54 functions as one of the four links of the constrained chain. The remaining two links are a front link 56 and a rear link 58. Those two links 56, 58 are provided at upper and lower ends thereof with couplers 562, 564; 582, 584, respectively, which are adapted to couple to other links, respectively. Both the front and rear links 56, 58 each have a laterally symmetrical configuration, and the upper and lower couplers 562, 582; 564, 584 each form one left and right pair. Accordingly, the front link 56 and the rear link 58 that are separately arranged in the front and rear directions, cooperate to surround the exterior of the knee joint 60, thereby defining an interior space thereof.

A hydraulic cylinder 70 that is drag generating means, is located in the interior space surrounded with the two links 56, 58. The hydraulic cylinder 70, as shown in FIG. 11C, comprises a cylinder main body 72 having an axis and including inside thereof a cylinder bore extending axially, a piston 74 movable into the cylinder bore and capable of defining the cylinder bore into two chambers and a piston rod 76 extending outside the cylinder main body 72 from the piston 74. The hydraulic cylinder 70 includes a known hydraulic circuit, not shown, supported within the cylinder main body 72 in order to produce a hydraulic resistance. The hydraulic circuit comprises a first passage including a first check valve for allowing only a flow from the first chamber toward the second chamber (this flow hereinafter referred to as the first-to-second flow) and a first throttle valve for rendering a flow resistance to the first-to-second flow, and a second passage including a second check valve for allowing only a flow from the second chamber to the first chamber (this flow hereinafter referred to as the second-to-first flow) and a second throttle valve for rendering a flow resistance to the second-to-first flow. By virtue of the foregoing arrangement, the hydraulic resistance at the time of bending and the hydraulic resistance at the time of extending can be separately established. The hydraulic cylinder 70 produces a torque as a drag, which torque is determined by a force caused by the hydraulic resistance and a product of this force and the length of a lever arm.

Figure 2A:
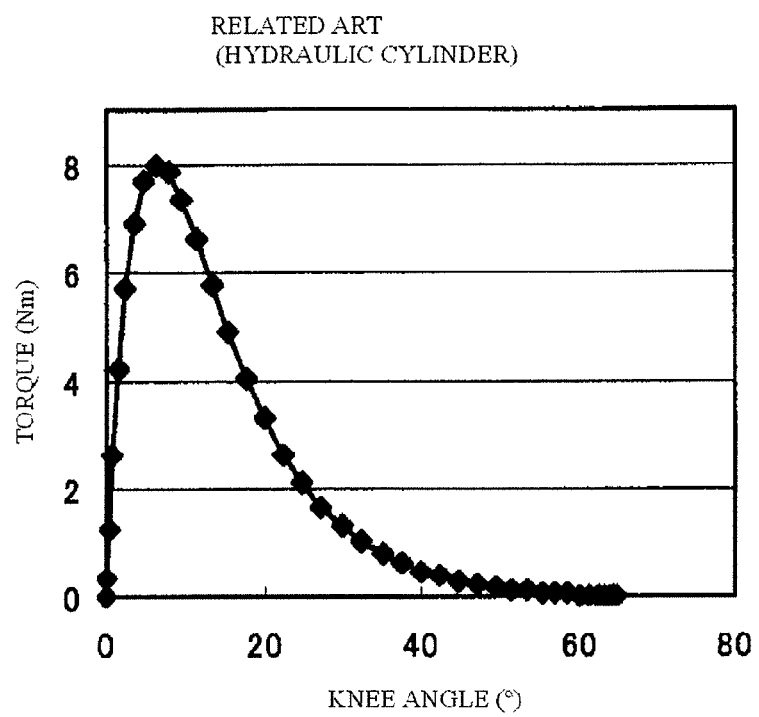
FIG. 2A shows characteristics obtainable between knee angle and torque in the conventional hydraulic cylinder.
Figure 2B:
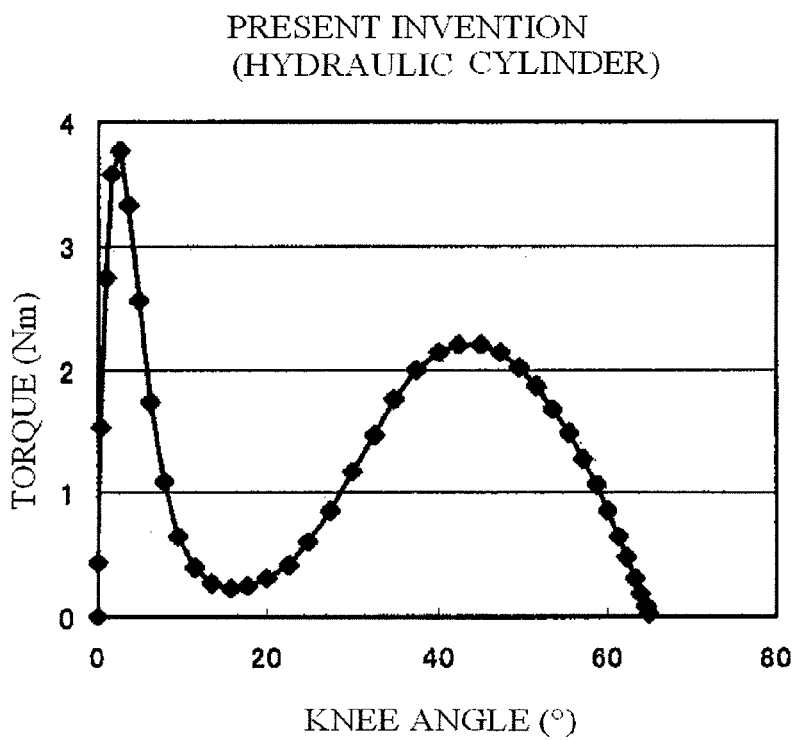
FIG. 2B shows characteristics obtainable between knee angle and torque in a hydraulic cylinder incorporated with the present invention.
Figure 3A:
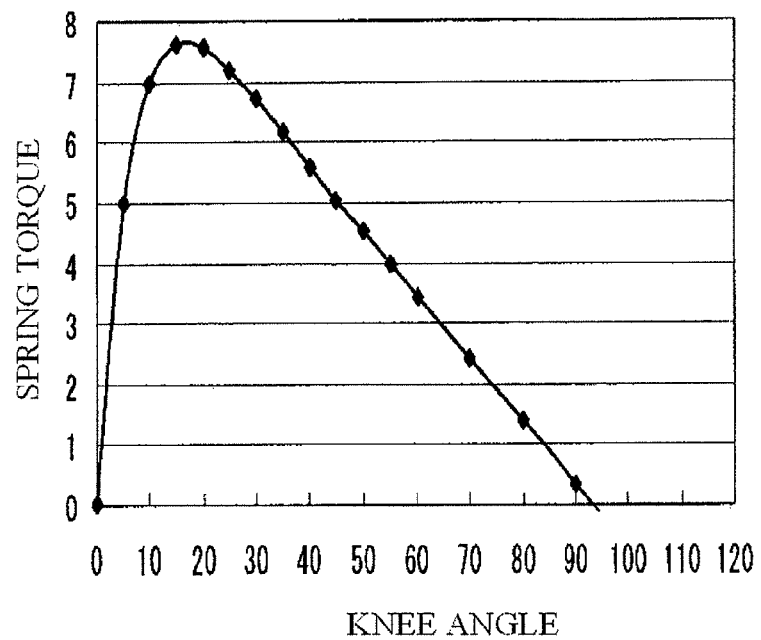
FIG. 3A shows characteristics obtainable between knee angle and torque in the conventional spring cylinder.
Figure 3B:
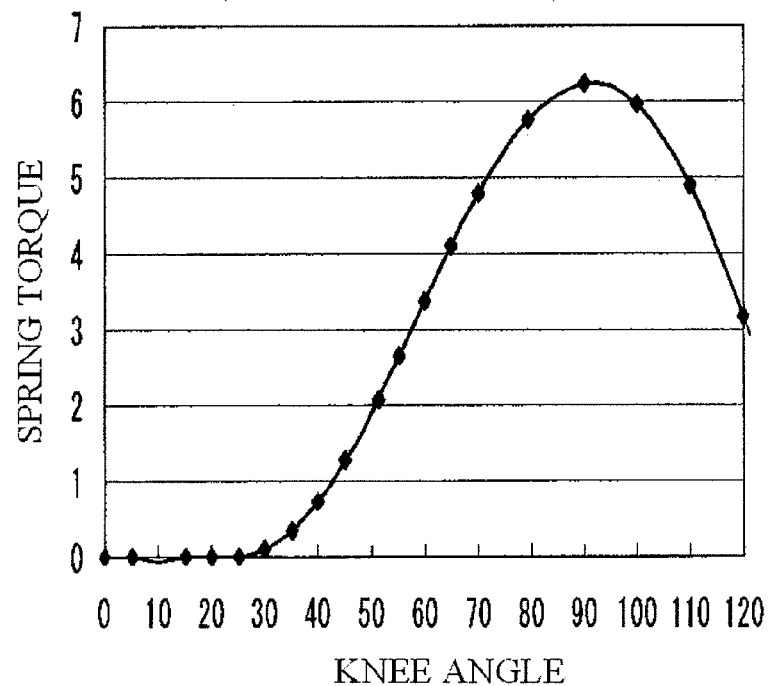
FIG. 3B shows characteristics obtainable between knee angle and torque in a spring cylinder incorporated with the present invention.
Figure 4:
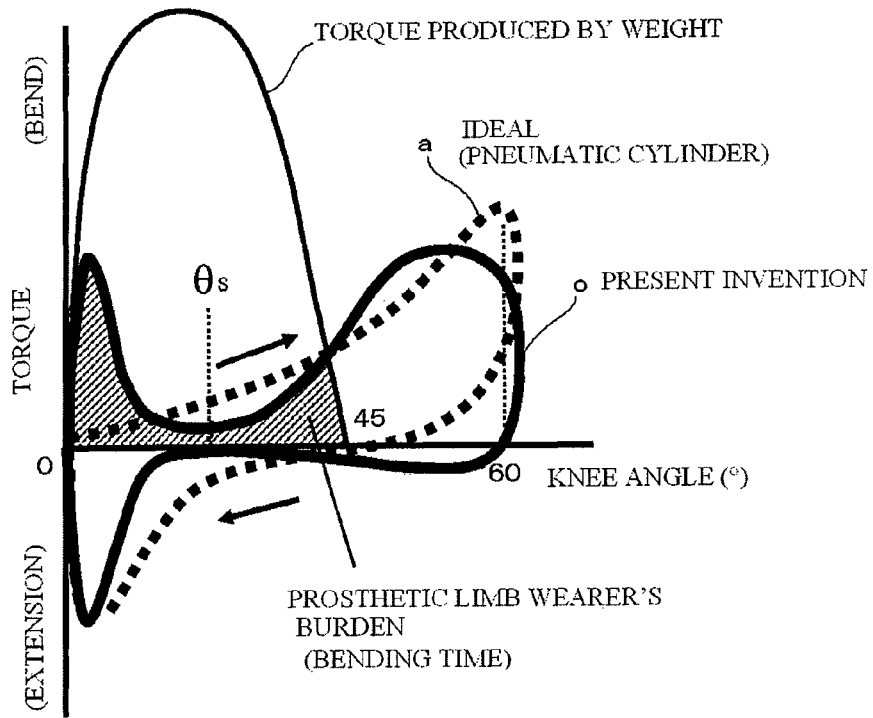
FIG. 4 is a characteristic diagram for explaining the present invention.
Figure 5:
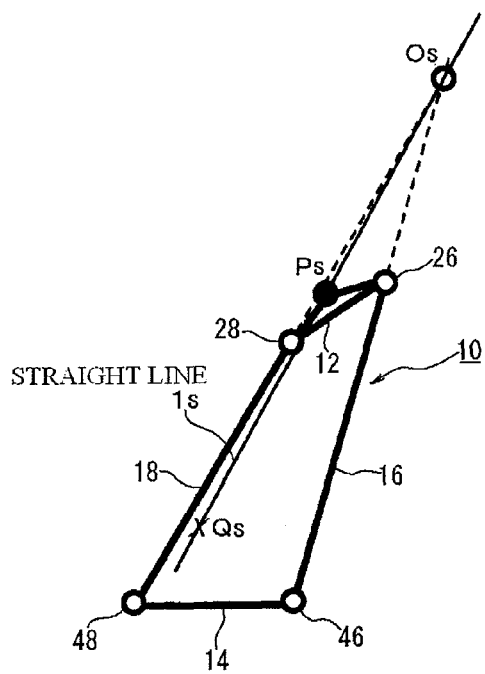
FIG. 5 is a view for diagrammatically explaining the first method for specifying the arrangement according to the present invention.
Figure 6A:
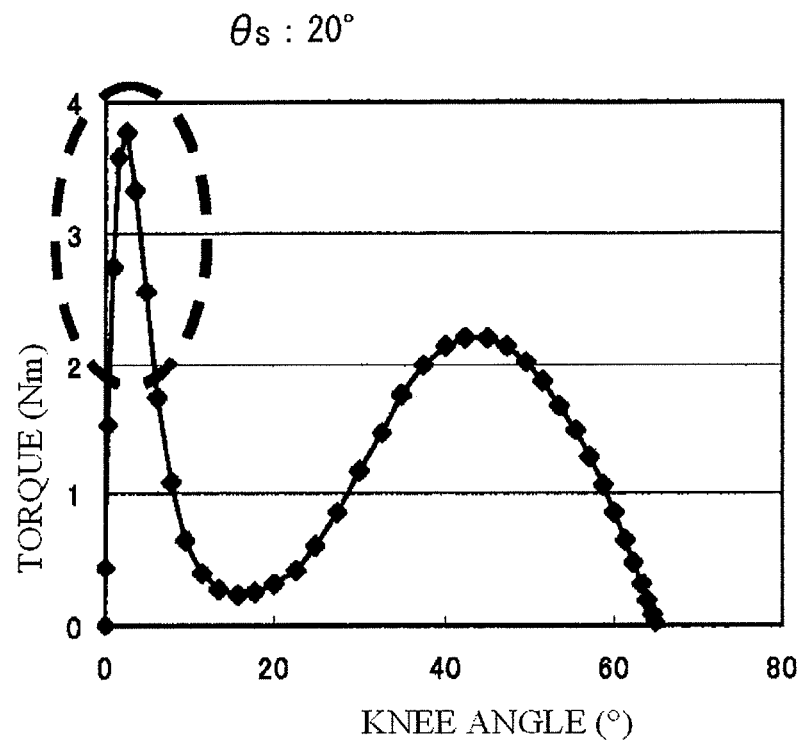
FIG. 6A shows the characteristics obtainable when the bending angle θs is set approximately to a normal angle 20°.
Figure 6B:
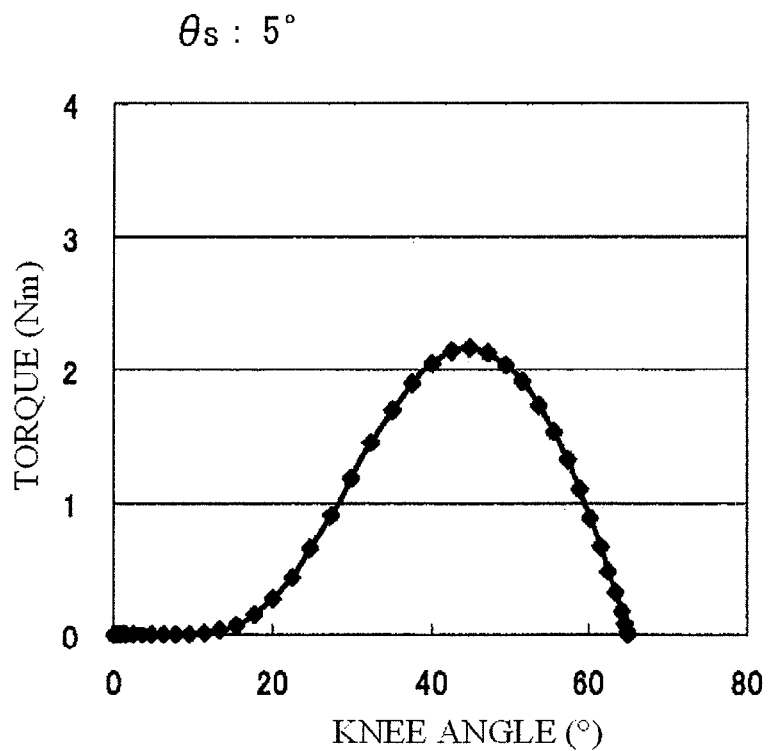
FIG. 6B shows the characteristics obtainable when the bending angle θs is set 5°.
Figure 7:
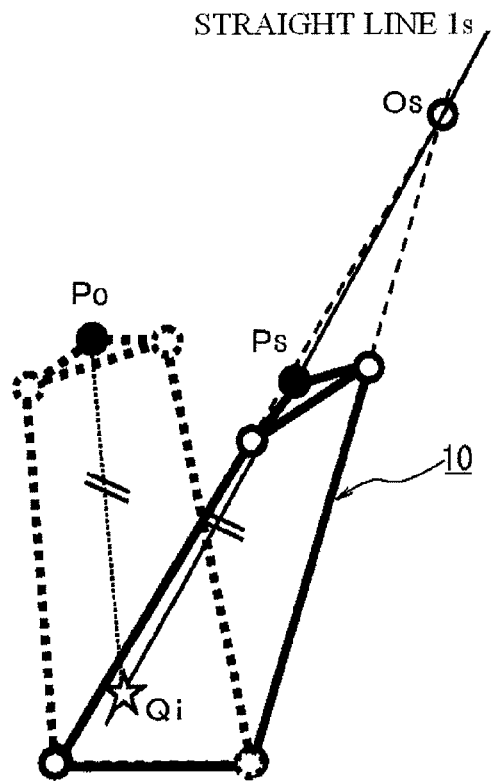
FIG. 7 is a view for diagrammatically explaining the second method for specifying the arrangement according to the present invention.
Figure 8:
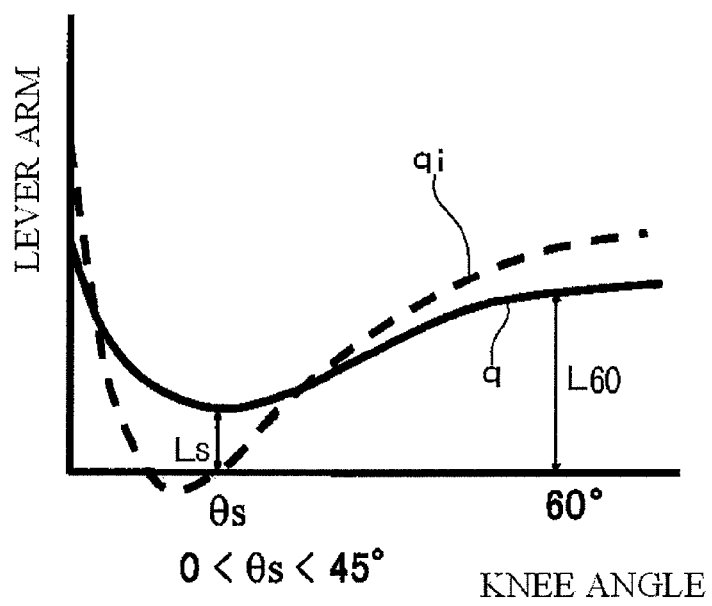
FIG. 8 shows one example of the characteristics between knee angle and lever arm length obtainable by the present invention.
Figure 9:
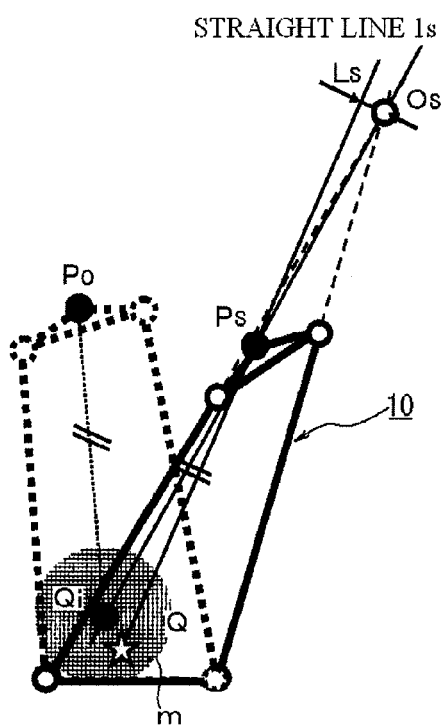
FIG. 9 is a view for diagrammatically explaining the third method for specifying the arrangement according to the present invention.
Figure 10A:
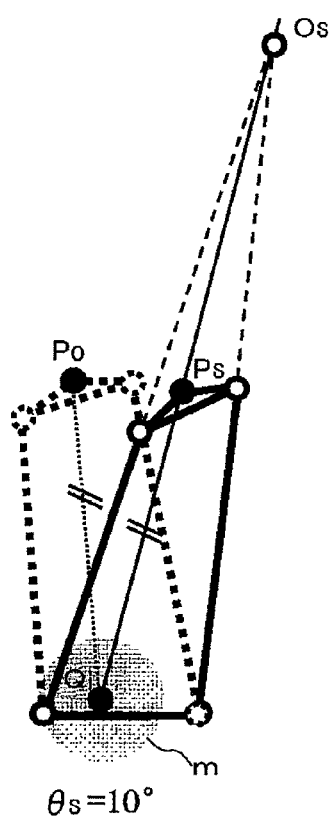
FIG. 10A shows the mesh section when the bending angle θs is 10°.
Figure 10B:
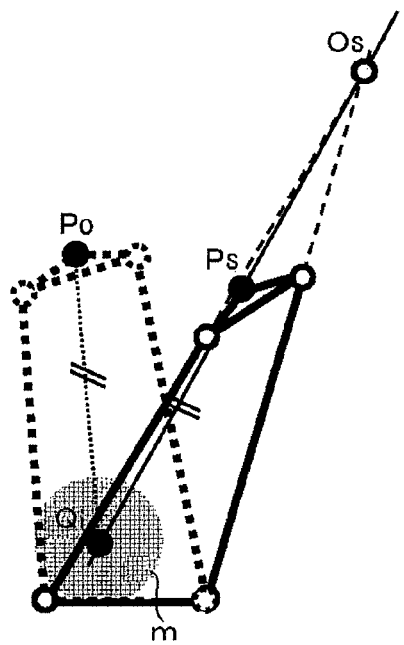
FIG. 10B shows the mesh section when the bending angle θs is 20°.
Figure 10C:
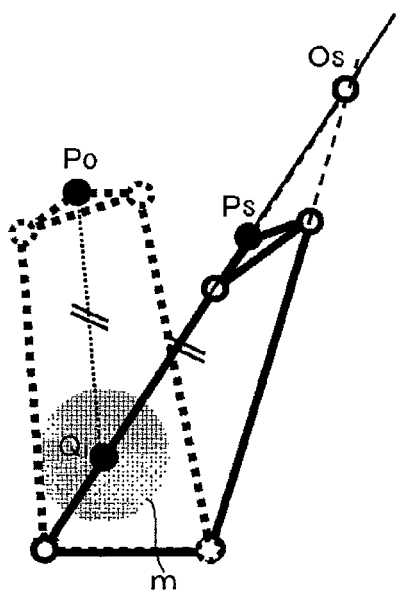
FIG. 10C shows the mesh section when the bending angle θs is 30°.

In this embodiment, an upper attachment position Ps and a lower attachment position Qs of the hydraulic cylinder 70 are established in accordance with the second method mentioned above, so that the characteristics shown in FIG. 2B can be obtained. The upper attachment position Ps is a portion between the front and rear couplers 562, 582 on the upper member 52 and located almost at the same height position as those couplers 562, 582. On the other hand, a lower attachment position Qs is a portion between the couplers 564, 584 but it is located at a height position above the couplers 564, 584. Accordingly, the lower member 54 includes an arm part erected upward. In order to make the hydraulic cylinder 70 pivotable with respect to the upper member 52 and the lower member 54, the hydraulic cylinder 70 is, of course, coupled by pivot at the upper attachment position Ps and the lower attachment position Qs.

FIGS. 12A through 12C and FIGS. 13A through 13C show the bending states of the above knee prosthesis 50 when the bending angles are 20°, 40° and 60°, respectively. It will be understood from those Figures that the above knee prosthesis 50 incorporated with the present invention can provide a comfortable sense of feel to its wearer in characteristics between knee angle and torque and yet, the construction and movement are simple.

MODIFIED EMBODIMENT

Figure 14:
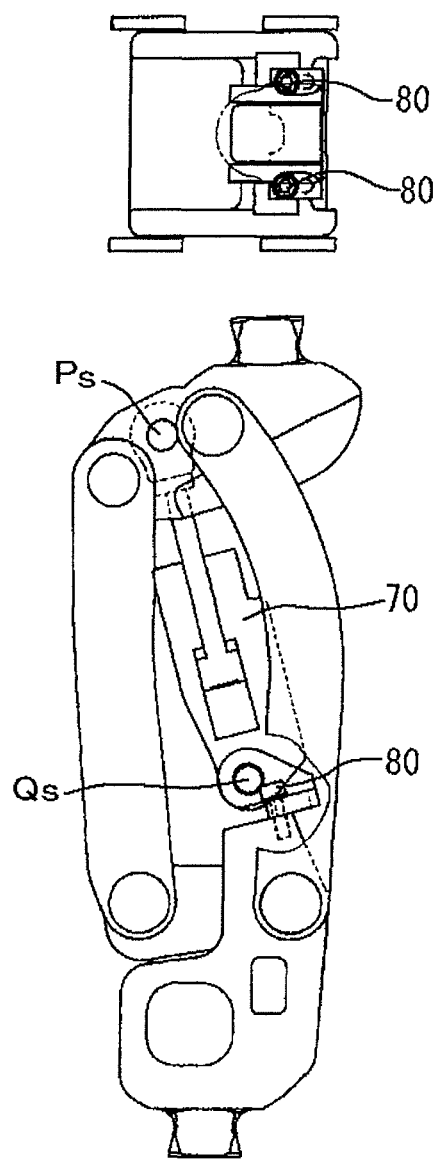
FIG. 14 is a modified embodiment of a prosthetic limb according to the present invention, showing an attachment state in the first position.
Figure 15:
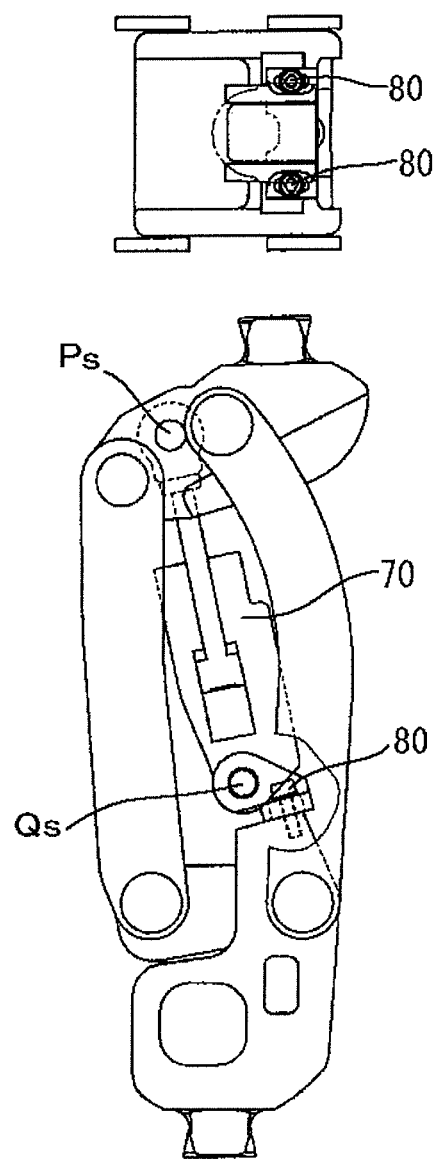
FIG. 15 is the modified embodiment of FIG. 14, but showing an attachment state in the second position.
Figure 16:
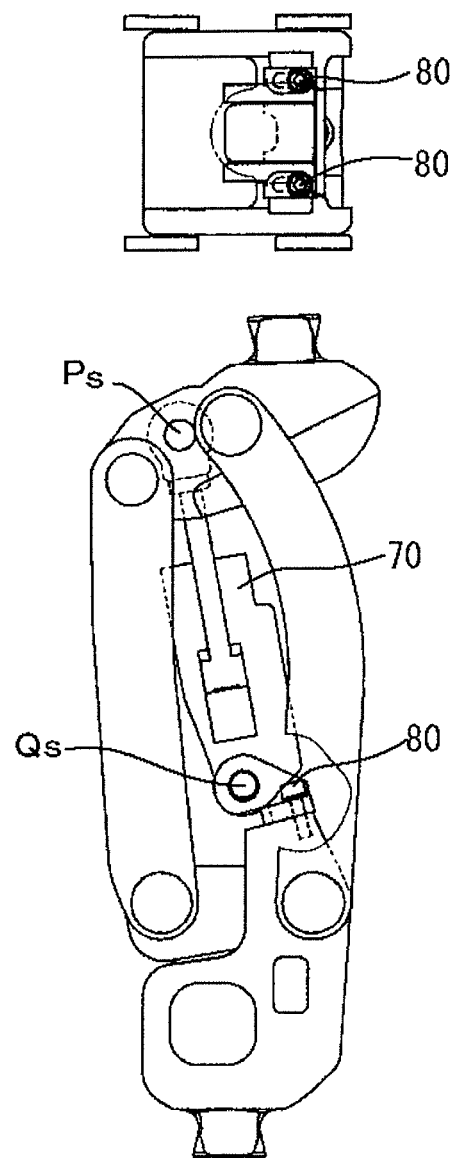
FIG. 16 is the modified embodiment of FIG. 14, but showing an attachment state in the third position.

In the above knee prosthesis according to the above-mentioned embodiment, the lower attachment position Qs of the hydraulic cylinder 70 is fixed at a single spot. It is also accepted, however, that means for adjusting the lower attachment position Qs is disposed on the above knee prosthesis, so that the torque in the initial period of bend of knee joint and the torque in the final period of bend of knee joint are balanced by adjustment. With the provision of the position adjusting means, a prosthetist or the like can externally adjust the attachment position of the above knee prosthesis in accordance with the choice of the prosthetic limb wearer. FIGS. 14 through 16 show one modified embodiment in which the prosthetic limb is provided with a fixing portion at three fixing spots fixable by bolts 80 and disposed in adjacent relation in a front and rear direction of the prosthetic limb. By properly selecting the three fixing spots, the lower attachment position Qs of the hydraulic cylinder 70 can be adjusted in the front and rear direction. The width of position adjustment is, for example, in a range of from 0 mm to 20 mm, and normally in a range of from 0 mm to 10 mm.

It is also accepted that a spring is used in combination with the hydraulic cylinder which is employed in the prosthetic limb of the above-mentioned embodiment. Although the operating fluid for the hydraulic cylinder utilized in the prosthetic limb of the above-mentioned embodiment is oil that is an incompressible fluid, other incompressible fluid such as water, may be used. It is also accepted that a highly compressed air having highly incompressible properties, for example, a highly compressed air higher by several times than the atmosphere is used.

Figure 17:
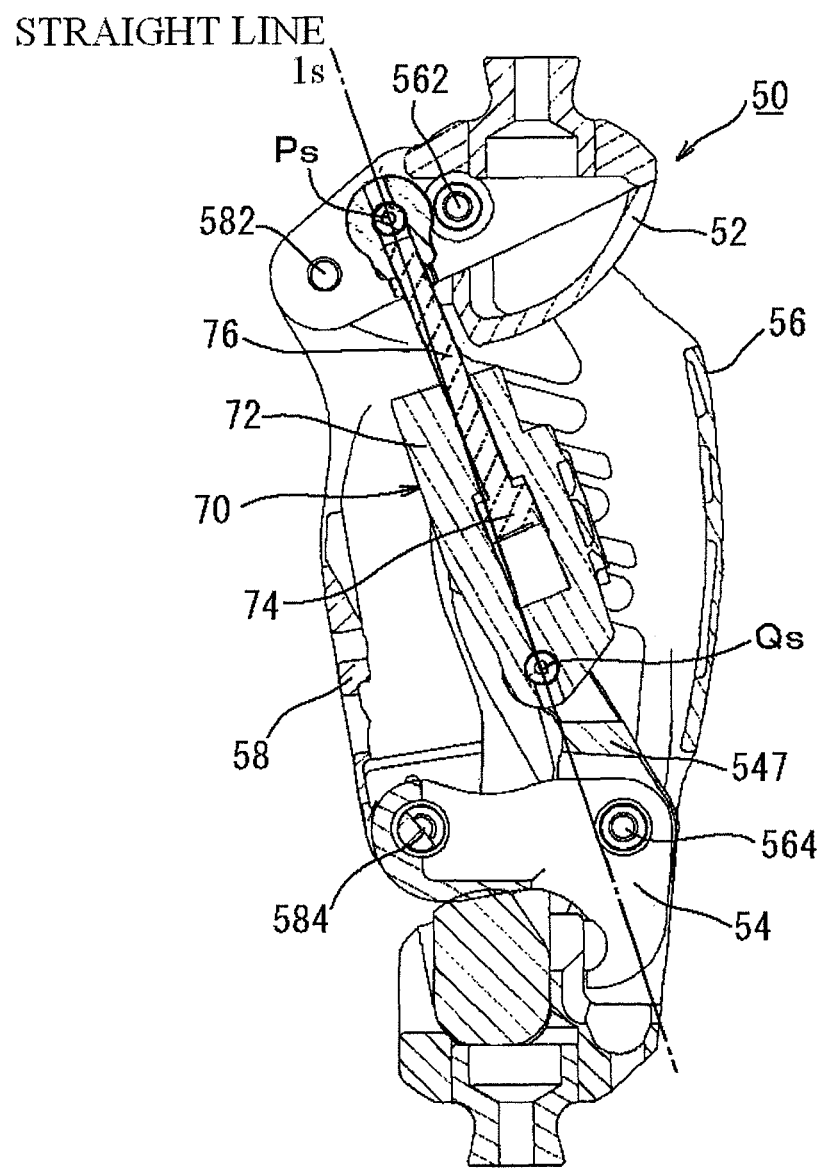
FIG. 17 is a view showing one example wherein the axis of a hydraulic cylinder is. shifted.

Moreover, the axis of the piston 74 and piston rod 76 of the hydraulic cylinder 70 may be deviated, where necessary in view of space, from a straight line $1s$ passing through the upper attachment position Ps and lower attachment position Qs of the hydraulic cylinder 70 (i.e., the straight line $1s$ and the axis are intersected at a small angle) as shown in FIG. 17. In that case, the attachment position of the hydraulic cylinder 70 must satisfy the above-mentioned conditions.

The invention claimed is:

1. A prosthetic limb comprising a knee joint composed of a multiple-link mechanism and adapted to make an upper member and a lower member movable about an instantaneous rotational center of rotation, and drag generating means composed of a hydraulic cylinder or a spring cylinder, said drag generating means being pivotably attached to said multiple-link mechanism and adapted to produce a drag for restraining deformation of said multiple-link mechanism, said drag generating means being in a specific arrangement with respect to said multiple-link mechanism, accordingly, during the swing phase of one cycle of a walking form, a relation of T1<T2 being satisfied wherein T1 is the first torque about the instantaneous center of rotation at the first stage of initial period of bend of knee joint and T2 is the second torque about the instantaneous center of rotation at the second stage of final period of the further advanced bend of knee joint, and wherein said drag generating means is in such an arrangement that the length L1 of a lever arm at the first stage of initial period of bend of knee joint is smaller than the length L2 of a lever arm at the second stage of final period of bend of knee joint, wherein the bend of knee joint comprises a bending angle, wherein said multiple-link mechanism comprises a constrained chain comprising at least four links rotatably coupled to each other at a fixed separation distance, wherein said upper and lower members are one of the links which compose said multiple-link mechanism, and said drag generating means is attached to said multiple-link mechanism at two positions, an upper attachment position with respect to said upper member and a lower attachment position with respect to said lower member, wherein the upper attachment position of said drag generating means is located on a line, or on an extension of the line, which line connects said upper and lower attachment positions with the instantaneous center of rotation when the bending angle at the first stage of initial period of bend of knee joint is arbitrary.

2. A prosthetic limb according to claim 1, wherein:

a large bending angle θs and a small bending angle θo that is smaller than the angle θs are selected at the first stage of initial period of bend of knee joint, and the lower attachment position of said drag generating means is set to a point, which point is located on an extension of a line that connects an upper member attachment position Ps at the large bending angle θs with the instantaneous center Os of rotation of said knee joint at the bending angle θs, and which point is also located at a point equidistant from the two positions, i.e., the upper attachment position Ps of said drag generating means at the large bending angle θs and the upper attachment position Po of said drag generating means with respect to said upper member at the small bending angle θo that is smaller than the angle θs.

3. A prosthetic limb according to claim 1, further comprising a position adjusting means for adjusting either the upper attachment position with respect to said upper member or the lower attachment position with respect to said lower member.

4. A prosthetic limb according to claim 3, wherein the first torque T1 about the instantaneous center of rotation at the first stage of initial period of bend of knee joint and the second torque T2 about the instantaneous center of rotation at the second stage of final period of the further advanced bend of knee joint are balanced by said position adjusting means.

5. A prosthetic limb according to claim 1, wherein said multiple-link mechanism includes at least a front link and a rear link, said front link is located on a front side of the knee and rotatably coupled to said upper member, and said rear link is located on a rear side of the knee and rotatably coupled to said lower member.

6. A prosthetic limb according to claim 1, wherein the knee angle at the first stage of initial period of bend of knee joint is in a range of from 0° to 45°, while the knee angle at the second stage of final period of bend of knee joint is in a range of from 45° to 60°.

7. A prosthetic limb according to claim 1, wherein the hydraulic cylinder that is said drag generating means, comprises a cylinder main body having an axis and including a cylinder bore that is formed inside said cylinder main body and disposed along said axis, a piston movable into said cylinder bore and adapted to axially define said cylinder bore into a first and a second chamber, and a piston rod extending outside said cylinder main body from said piston.

* * * * *